(12) United States Patent
Kalnes et al.

(10) Patent No.: US 9,567,534 B2
(45) Date of Patent: Feb. 14, 2017

(54) FLEXIBLE GASOLINE PROCESS USING MULTIPLE FEEDSTOCKS

(71) Applicant: UOP LLC, Des Plaines, IL (US)

(72) Inventors: Tom N. Kalnes, LaGrange, IL (US); Stuart Smith, Lake Zurich, IL (US); Mary Wier, Schaumburg, IL (US); Alakananda Bhattacharyya, Glen Ellyn, IL (US); Hayim Abrevaya, Kenilworth, IL (US)

(73) Assignee: UOP LLC, Des Plaines, IL (US)

( * ) Notice: Subject to any disclaimer, the term of this patent is extended or adjusted under 35 U.S.C. 154(b) by 289 days.

(21) Appl. No.: 14/257,812

(22) Filed: Apr. 21, 2014

(65) Prior Publication Data
US 2015/0299584 A1    Oct. 22, 2015

(51) Int. Cl.
| | | |
|---|---|---|
| *C10G 35/06* | (2006.01) | |
| *C10G 35/04* | (2006.01) | |
| *C10G 35/085* | (2006.01) | |
| *C10G 35/09* | (2006.01) | |
| *C10G 35/095* | (2006.01) | |

(Continued)

(52) U.S. Cl.
CPC ............. *C10G 35/06* (2013.01); *C07C 5/2797* (2013.01); *C07C 6/10* (2013.01); *C10G 35/04* (2013.01); *C10G 35/065* (2013.01); *C10G 35/085* (2013.01); *C10G 35/09* (2013.01); *C10G 35/095* (2013.01); *C07C 2527/125* (2013.01); *C07C 2531/02* (2013.01); *C10G 2300/104* (2013.01); *C10G 2300/1044* (2013.01); *C10G 2400/02* (2013.01)

(58) Field of Classification Search
CPC ......... C10G 35/06; C10G 59/06; C10G 35/65; C10G 35/85; C10G 35/95; C10G 35/04; C10G 2300/104; C10G 2300/1044; C10G 2400/02; C07C 6/00; C07C 6/08; C07C 6/10; C07C 5/2797; C07C 2527/125; C07C 2531/02; C07C 5/23; C07C 5/25; C07C 5/2506; C07C 5/2512; C07C 5/2518; C07C 5/2525; C07C 5/2543; C07C 5/255
USPC ........ 585/734, 735, 736, 737, 738, 739, 708
See application file for complete search history.

(56) References Cited

U.S. PATENT DOCUMENTS

| | | | | |
|---|---|---|---|---|
| 2,583,740 | A | * | 1/1952 | Kemp .................. C07C 5/2786 585/736 |
| 3,280,022 | A | * | 10/1966 | Engel .................... C10G 61/06 585/317 |

(Continued)

OTHER PUBLICATIONS

Schmidt et al. "Disproportionation of light paraffins," Energy & Fuels (2008), 22 (3), 1812-1823.

*Primary Examiner* — Sharon Pregler (57) ABSTRACT

A flexible process for gasoline refineries is described. The process can vary depending on the available feedstock and the desired products. At one time, the process can involve disproportionating pentanes to a product mixture including isobutane and isohexane. At other times, by switching the feedstock and operating conditions, the process can convert a mixture of $C_4$ and $C_7$ paraffins to a low aromatic blendstock with suitable octane and a vapor pressure lower than butanes. The process can be performed in separate standalone units operated at different times, or a single unit can be operated according to one process at one time and according to the other process at another time.

20 Claims, 2 Drawing Sheets

(51) Int. Cl.
*C07C 5/27* (2006.01)
*C07C 6/10* (2006.01)

(56) References Cited

U.S. PATENT DOCUMENTS

| | | |
|---|---|---|
| 3,668,269 A | 6/1972 | Chloupek |
| 3,676,522 A | 7/1972 | Sieg |
| 3,793,251 A | 2/1974 | Hughes |
| 3,864,417 A | 2/1975 | Hughes |
| 4,025,577 A | 5/1977 | Siskin et al. |
| 4,929,793 A | 5/1990 | Morrison |
| 5,396,016 A | 3/1995 | Jablonski et al. |
| 6,423,880 B1 | 7/2002 | Randolph et al. |
| 6,797,853 B2 * | 9/2004 | Houzvicka ............ C07C 5/2721 585/741 |
| 7,053,261 B2 | 5/2006 | Herbst et al. |
| 7,214,845 B2 | 5/2007 | Randolph et al. |
| 7,902,418 B2 | 3/2011 | Schmidt et al. |
| 2002/0002318 A1 | 1/2002 | O'Rear et al. |

* cited by examiner

FLEXIBLE GASOLINE PROCESS USING MULTIPLE FEEDSTOCKS

BACKGROUND OF THE INVENTION

High octane gasoline is required for modern gasoline engines. Previously, it was common to achieve octane number improvement by the use of various lead-containing additives. As lead has been phased out of gasoline for environmental reasons, it has become increasingly necessary to rearrange the structure of the hydrocarbons used in gasoline blending in order achieve higher octane ratings. Catalytic reforming and catalytic isomerization are two widely used processes for this upgrading.

The traditional gasoline blending pool normally includes $C_4$ and heavier hydrocarbons having boiling points of less than 205° C. (400° F.) at atmospheric pressure. This range of hydrocarbons includes $C_4$-$C_6$ paraffins, and especially the $C_5$ and $C_6$ normal paraffins which have relatively low octane numbers. The $C_4$-$C_6$ hydrocarbons have the greatest susceptibility to octane improvement by lead addition and were formerly upgraded in this manner. With the phase out of lead additives, octane improvement was obtained by using isomerization to rearrange the structure of the paraffinic hydrocarbons into branched-chain paraffins or reforming to convert the $C_6$ and heavier hydrocarbons to aromatic compounds. Normal $C_5$ hydrocarbons are not readily converted into aromatics; therefore, the common practice has been to isomerize these lighter hydrocarbons into corresponding branched-chain isoparaffins. Although the $C_6$ and heavier hydrocarbons can be upgraded into aromatics through dehydrocyclization, the conversion of $C_6$ hydrocarbons to aromatics creates higher density species and increases gas yields with both effects leading to a reduction in liquid volume yields. Moreover, the health concerns related to benzene have lead to restrictions on benzene and aromatics. Therefore, it is preferred to change the $C_6$ paraffins to an isomerization unit to obtain $C_6$ isoparaffin hydrocarbons. Consequently, octane upgrading commonly uses isomerization to convert $C_6$ and lower boiling hydrocarbons.

The Reid vapor pressure (RVP) of gasoline has been utilized by the Environmental Protection Agency as a means of regulating volatile organic compounds emissions by transportation fuels and for controlling the formation of ground level ozone. As these regulations become more stringent and as more ethanol (which has a high vapor pressure) is blended into gasoline, $C_5$ paraffins need to be removed from the gasoline pool. Moreover, the need to remove components may also extend to some $C_6$ paraffins. This may result in refiners being oversupplied with $C_5$ paraffins and possibly $C_6$ paraffins, forcing them to sell these products at prices lower than gasoline blendstock.

Commercial refiners face a number of problems utilizing hydrocarbons with molecular weights less than about 90 in gasoline. Some refiners are limited in the amount of light naphtha, particularly pentanes, they can add to gasoline in the summer months because of more stringent regulations on vapor pressure. In addition, some refiners cannot blend all of the high octane reformate they produce into gasoline because of new regulations limiting the total aromatics to 35 vol %. The growth of shale crude oil production has increased the amount of low value butanes and pentanes produced in refineries. Finally, some refiners need to purchase isobutane as feedstock for $C_3$ and $C_4$ olefin conversion to gasoline in existing alkylation units.

Therefore, there is a need for processes which allow better utilization of light and heavy naphtha in refineries.

SUMMARY OF THE INVENTION

One aspect of the invention is a process for refining naphtha. In one embodiment, the process includes different operation during first and second time periods. During the first time period, a hydrotreated heavy naphtha feed is separated into a $C_7$-rich fraction and a $C_8$+-rich fraction in a first separation zone. The $C_7$-rich fraction is introduced into a first reaction zone, and a stream comprising $C_4$ paraffins is also introduced into the first reaction zone. A first portion of the $C_7$-rich fraction is disproportionated by contacting the first portion of the $C_7$-rich fraction with a first catalyst in the reaction zone and a second portion of the $C_7$-rich fraction and the $C_4$ paraffins are reverse disproportionated by contacting the second portion of the $C_7$-rich fraction and the $C_4$ paraffins with the first catalyst in the first reaction zone under first reaction conditions suitable for disproportionation and reverse disproportionation to form a first reaction product mixture. The first reaction product mixture is separated in a second separation zone into at least a $C_{3-}$-rich stream, an iso-$C_4$-rich stream, and a $C_{6+}$-rich stream. The $C_{6+}$-rich stream is introduced into a first hydrocarbon pool. During a second time period, a light naphtha feed is separated into a $C_5$-rich fraction and a $C_6$-rich fraction. The $C_5$-rich fraction is introduced into a second reaction zone. The $C_5$-rich fraction is disproportionated by contacting the $C_5$-rich fraction with a second catalyst in the second reaction zone under second reaction conditions to form a second reaction product mixture. The second reaction product mixture is separated into at least an iso-$C_4$-rich stream, and a $C_{6+}$-rich stream in a third separation zone. The $C_{6+}$-rich stream is introduced into a second hydrocarbon pool.

DETAILED DESCRIPTION OF THE INVENTION

The present invention meets this need by providing a flexible process for gasoline refineries. The process can vary depending on the available feedstock and the desired products.

At one time, for example in summer, the process can involve disproportionating unwanted pentanes to a product mixture comprising $C_{4-}$ and $C_{6+}$ hydrocarbons. The process forms primarily isoparaffins, and very few naphthenes, aromatics, and alkenes are formed. The flexible process can convert pentanes to isohexane and isobutane-rich products. The isobutane-rich product formed can be converted to low RVP gasoline blendstock by reaction with propylenes and butenes in a downstream alkylation unit. The isohexane-rich product has good octane and a lower RVP than pentane. In some cases, the process also produces an isopentane-rich co-product.

Butanes can also be upgraded into a $C_{5+}$ fraction in the presence of a heavier paraffinic feed. For example, in winter, by switching the feedstock and operating conditions, the process can convert a mixture of butanes and heptanes to a low aromatic gasoline blendstock with suitable octane and a vapor pressure lower than butanes.

The processes can be performed in separate stand-alone units operated at different times, or a single unit can be operated according to one process at one time and according to the other process at another time.

Figure 1:
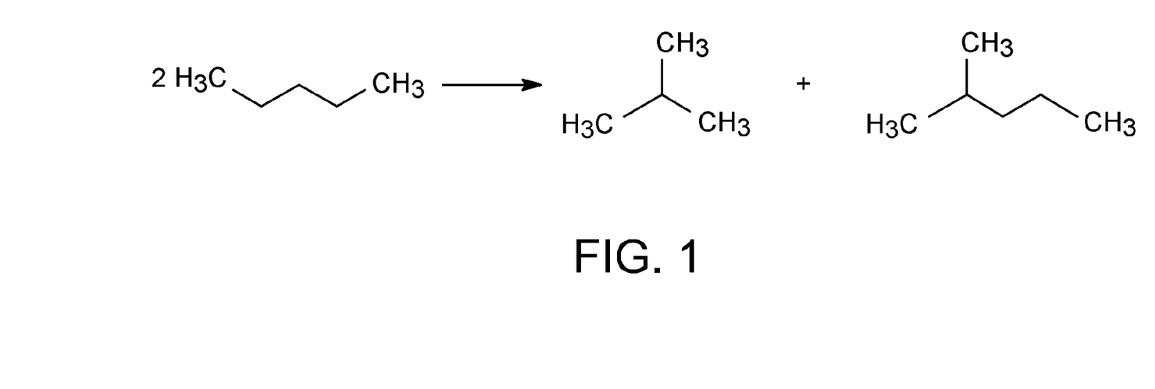
FIG. 1 illustrates the disproportionation reaction of n-pentane.

The disproportionation of paraffins (e.g., n-pentane (n-$C_5$)) involves reacting two moles of hydrocarbon to form one mole each of two different products, one having a carbon count greater than the starting material and the other having a carbon count less than the starting material, as shown in FIG. 1. The total number of moles in the system remains the same throughout the process, but the products have different carbon counts from the reactants.

Figure 2:
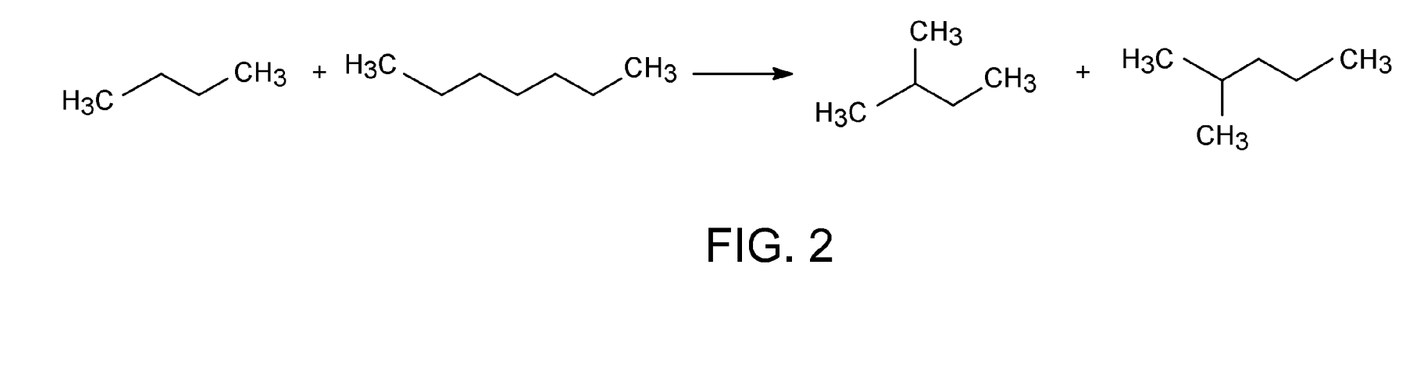
FIG. 2 illustrates the reverse disproportionation reaction of n-butane and n-heptane.
Figure 3:
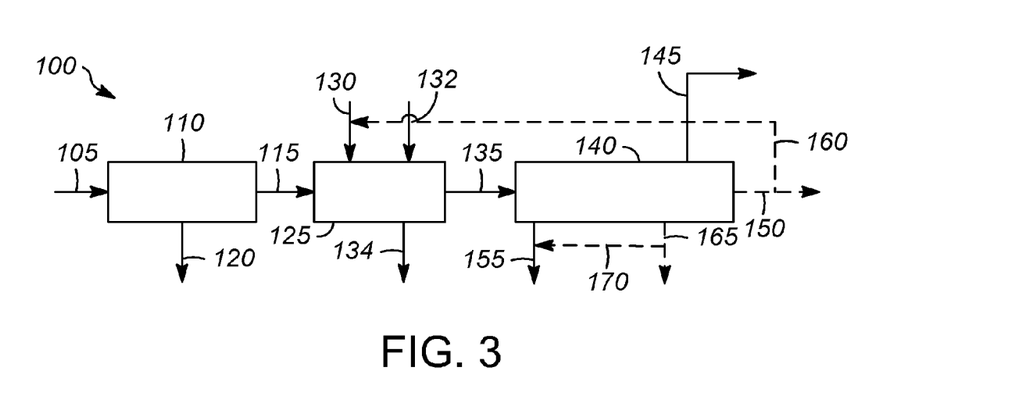
FIG. 3 illustrates one embodiment of a disproportionation and reverse disproportionation process.

The microscopic reverse of pentane disproportionation is the combination of one mole of hexane and one mole of butane to form two moles of pentane. This type of reaction is referred to herein as reverse disproportionation. Reverse disproportionation-type reactions can occur in which two paraffins having different carbon numbers react to form two different paraffins having different carbon numbers from those of the feed where the total number of moles of product and moles of carbon and hydrogen in the products does not change from the total number in the feed (e.g., pentane and octane reacting to form hexane and heptane). These reactions are sometimes referred to as comproportionation or molecular averaging reactions. These paraffin rearrangements have also been called alkane metathesis. The use of any of these terms is meant to illustrate that paraffins can react with other paraffins to form additional paraffins different from the original feed. Another example of reverse disproportionation involves heptane and butane reacting to form pentane and hexane, as illustrated in FIG. 2. Utilizing the equilibrium among the various species, the concentration of the product can be controlled by varying the relative ratios of the species. Consequently, two different paraffinic feed sources of varying carbon count can be reacted to obtain a product containing paraffins of intermediate carbon count. FIG. 3 illustrates the disproportionation and reverse disproportionation process 100 which involves upgrading butanes to $C_{5+}$ hydrocarbons. This process reduces the amount of feed going to the reformer. It also results in a lower fraction of aromatics in the gasoline.

A hydrotreated heavy naphtha feed 105 is used. Heavy naphtha is a hydrocarbon mixture typically comprising seven, eight and nine carbon hydrocarbon molecules with the majority of the hydrocarbon molecules being saturates as opposed to unsaturates. Heavy naphtha is often defined by a nominal boiling point range of about 71° C. (160° F.) to about 204° C. (400° F.), or about 82° C. (180° F.) to about 204° C. (400° F.), or about 93° C. (200° F.) to about 182° C. (360° F.). Carbon chain length can extend from $C_6$-$C_{10}$ in the broadest sense depending on how the distillation column operates.

The hydrotreated heavy naphtha feed can be formed by separating a full range naphtha feed into a light naphtha stream and a heavy naphtha stream in a naphtha splitter, for example. Hydrotreated full range naphtha is a hydrocarbon mixture typically comprising five, six, seven, eight and nine carbon hydrocarbon molecules with the majority of the hydrocarbon molecules being saturates as opposed to unsaturates. Hydrotreated full range naphtha typically has less than about 10 wt-ppm sulfur and less than 1 wt-ppm nitrogen. Full range naphtha is often defined by a nominal boiling point range about 21° C. (70° F.) to about 204° C. (400° F.), or about 27° C. (80° F.) to about 182° C. (360° F.). Carbon chain length can extend from $C_4$-$C_{10}$ in the broadest sense depending on how the distillation column operates.

The hydrotreated heavy naphtha feed 105 is sent to a separation zone 110 where it is separated into a $C_7$-rich fraction 115 and a $C_{8+}$-rich fraction 120. The separation can take place in a heavy naphtha splitter, for example.

The $C_{8+}$-rich fraction 120 (e.g., with a boiling point range of about 99° C. (210° F.) to about 204° C. (400° F.)), which can include some aromatic compounds, can be sent to a reformer for further processing as discussed below, and the reformate can be sent to a hydrocarbon pool, such as a gasoline pool.

The $C_7$-rich fraction (e.g., with a boiling point range of about 82° C. (180° F.) to about 99° C. (210° F.)) 115 is sent to reaction zone 125. A stream 130 comprising $C_4$ paraffins is also introduced into the reaction zone 125. The $C_4$ paraffins can include n-$C_4$ paraffins, iso-$C_4$ paraffins, or mixtures thereof. In some embodiments, a liquid catalyst stream 132 is also introduced into the reaction zone 125. In other embodiments, the catalyst will be contained in the reaction zone.

A portion of the $C_7$-rich fraction is contacted with a catalyst in the reaction zone 125 and disproportionated. The $C_4$ paraffins and at least a second portion of the $C_7$-rich fraction are contacted with the catalyst in the reaction zone 125 and reverse disproportionated. By a portion of the $C_7$-rich fraction we mean that some of the $C_7$-rich fraction reacts in the stated way. The portions are not physically separated. There will also be some disproportionation of the $C_4$ paraffins. Other reactions may also occur, such as isomerization of the various paraffins. If the $C_4$ paraffins are present in excess of their equilibrium amount, equilibrium favors the reverse disproportionation reaction.

The molar ratio of $C_4$ to $C_7$ is at least about 0.055, or at least about 0.1, or at least about 0.2, or at least about 0.5, or at least about 0.75, or at least about 1, or at least about 5, or at least about 10, or at least about 15. As the $C_4$ to $C_7$ ratio increases, butanes are consumed and the reaction product becomes richer in pentanes and hexanes. If the ratio is too low, $C_4$ paraffins will be generated by disproportionation of $C_7$.

Where a liquid catalyst is used, a spent liquid catalyst stream 134 is removed from the reaction zone 125. It can be regenerated and recycled to the reaction zone 125.

The reaction mixture 135 includes the disproportionation products and reverse disproportionation products. The reaction mixture 135 is separated in a second separation zone 140 into at least a $C_{3-}$-rich stream 145, an iso-$C_4$-rich stream 150, and a $C_{6+}$-rich stream 155. Additional product streams can be taken, if desired. One example of a suitable separation process is distillation.

When a liquid catalyst is used, the liquid catalyst is also present in the reaction mixture. The liquid catalyst can be separated from the reaction mixture by phase separation due to the density difference between the hydrocarbons and the liquid catalyst before separation into the various hydrocarbon streams.

The $C_{3-}$-rich stream 145 can be recovered and further processed. The $C_{3-}$-rich stream can be used in a variety of processes. It can be used as a refinery fuel instead of natural gas. Alternatively, it could be purified and recovered as a high purity liquid propane product. It could be used as a feedstock for a hydrogen plant. It could also be used as a feedstock for a chemical plant, such as an ethylene cracker, although this would be less common.

The iso-$C_4$-rich stream 150 can be recovered. In some embodiments, a portion 160 of the iso-$C_4$-rich stream 150 is recycled to reaction zone 125 and used in the reverse disproportionation reaction. The iso-$C_4$-rich product can be used in alkylate production as discussed below In some embodiments, a n-$C_4$-rich stream is recovered and recycled to the reaction zone 125 (not shown).

The $C_{6+}$-rich stream 155 is sent to the hydrocarbon pool, such as a gasoline pool.

In some embodiments, the reaction mixture 135 is separated into at least a $C_3$-rich stream 145, an iso-$C_4$-rich stream 150, a $C_{6+}$-rich stream 155, and a $C_5$-rich stream 165, which can be recovered. In some embodiments, a portion 170 of the $C_5$-rich stream 165 is mixed with the $C_{6+}$-rich stream 155 and sent to the hydrocarbon pool. In some embodiments, all or a portion of the $C_5$-rich stream 165 could be recycled to the reaction zone 125 (not shown). Alternatively, all or a portion of the $C_5$-rich stream 165 could be recovered and used a feedstock for a chemical plant.

If a separate $C_5$-rich stream is not recovered, the $C_5$ hydrocarbons will be included in the $C_{6+}$-rich stream.

Figure 4:
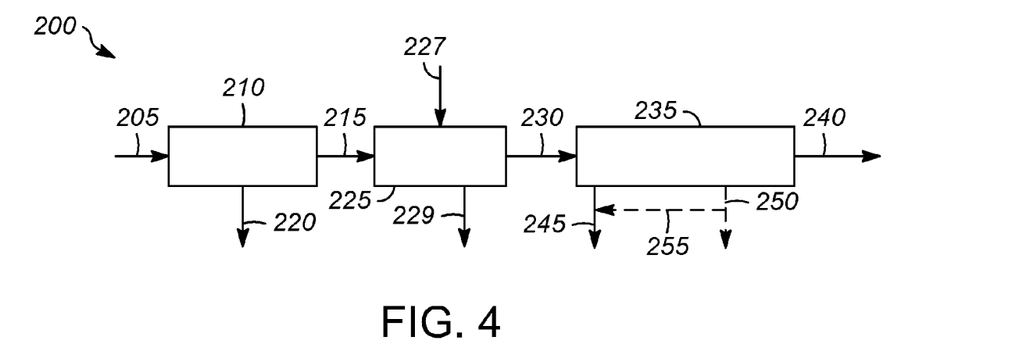
FIG. 4 illustrates one embodiment of a disproportionation process.

FIG. 4 illustrates the disproportionation process 200 used during the second time period. It involves conversion of pentanes and produces an iso-$C_4$-rich product and an iso-$C_6$-rich product. The iso-$C_4$-rich product can be used in alkylate production as discussed below. The iso-$C_6$-rich product has a RVP lower than that of $C_5$. These products enable greater production volumes of gasoline blendstock meeting summer volatility specifications.

A hydrotreated light naphtha feed 205 is used in this process. Light naphtha is a hydrocarbon mixture typically comprising five carbon and six carbon hydrocarbon molecules with the majority of these molecules being saturates as opposed to unsaturates. Light naphtha is often defined by a nominal boiling point range of about 21° C. (70° F.) to about 93° C. (200° F.), or about 27° C. (80° F.) to about 82° C. (180° F.). Carbon chain length can extend from $C_4$-$C_7$ in the broadest sense depending on how the distillation column operates.

The light naphtha feed 205 is sent to a separation zone 210 where it is separated into a $C_5$-rich fraction 215 and a $C_6$-rich fraction 220. The separation can take place in a light naphtha splitter, for example.

The $C_6$-rich fraction 220 can be isomerized as discussed below, and the isomerization product sent to a hydrocarbon pool, such as a gasoline pool.

The $C_5$-rich fraction is sent to reaction zone 225. When a liquid catalyst is used, a liquid catalyst stream 227 is also introduced into reaction zone 225. The $C_5$-rich fraction is contacted with a catalyst in the reaction zone 225 and disproportionated.

The spent liquid catalyst stream 229 is removed from reaction zone 225 if a liquid catalyst is used. It can be regenerated and recycled to the reaction zone 225.

The reaction mixture 230 includes the disproportionation products. The reaction mixture 230 is separated in a second separation zone 235 into at least an iso-$C_4$-rich stream 240, and a $C_{6+}$-rich stream 245. Additional product streams can be taken, if desired.

The liquid catalyst is also present in the reaction mixture if a liquid catalyst is used. The liquid catalyst can be separated from the reaction mixture by phase separation due to the density difference between the hydrocarbons and the liquid catalyst before separation into the various hydrocarbon streams.

The iso-$C_4$-rich stream 240 can be recovered. The $C_{6+}$-rich stream 245 is sent to the hydrocarbon portion of the gasoline pool.

In some embodiments, the reaction mixture 230 is separated into at least an iso-$C_4$-rich stream 240, a $C_{6+}$-rich stream 245, and a $C_5$-rich-stream 250, which can be recovered. In some embodiments, a portion 255 of the $C_5$-rich stream 250 is mixed with the $C_{6+}$-rich stream 245 and sent to the hydrocarbon portion of the gasoline pool. The $C_5$-rich stream 250 can also be recycled to the reaction zone (not shown), or it can be sold as a petrochemical feedstock. It could also be used as a fuel in the refinery, or as a secondary feedstock for a hydrogen plant.

If a separate $C_5$-rich stream is not recovered, the $C_5$ hydrocarbons will be included in the $C_{6+}$-rich stream.

In some embodiments, the vapor pressure of the $C_{6+}$-rich stream can be controlled by controlling the amount of the $C_5$-rich stream included in the $C_{6+}$-rich stream during at least one of the first or second time periods. By forming a separate $C_5$-rich stream and mixing only a portion of the $C_5$-rich stream (or none) with the $C_{6+}$-rich stream, the vapor pressure can be controlled as needed.

In some embodiments, the gasoline product yield can be maximized by mixing at least a portion of the $C_5$-rich stream with the $C_{6+}$-rich stream during at least one of the first or second time periods.

The iso-$C_4$-rich stream and at least one olefin containing stream (containing olefins such as an ethylene, propylene, or butene stream, or mixtures thereof) can be introduced into an alkylation reaction zone during at least one of the first or second time periods to produce additional gasoline blendstock.

Suitable first reaction conditions, second reaction conditions, or both include a temperature of about 200° C. or less, or about 175° C. or less, or about 150° C. or less, or about 125° C. or less, or about 100° C. or less, or about 90° C. or less, or about 80° C. or less, or about 70° C. or less, or about 60° C. or less, or in the range of about 0° C. to about 200° C., or about 0° C. to about 175° C., or about 0° C. to about 150° C., or about 10° C. to about 150° C., or about 25° C. to about 150° C., or about 30° C. to about 150° C., or about 40° C. to about 150° C., or about 50° C. to about 150° C., or about 55° C. to about 150° C.

The pressure in the reaction zone is typically in the range of about 0 MPa to about 13.8 MPa, or about 0 MPa to about 8.1 MPa, or about 0 MPa to about 5 MPa, or about 0 MPa to about 3.5 MPa. The pressure should be sufficient to ensure that the reaction product is in a liquid state. Small amounts of vapor may also be present, but this should be minimized.

The reaction can take place in the presence of a gas. Suitable gases include, but are not limited to methane, ethane, propane, hydrogen, hydrogen chloride, nitrogen and the like.

The residence time in the reaction zone is generally less than about 12 hr, or less than about 10 hr, or less than 7 hr, or less than 5 hr, or less than 4 hr, or less than 3 hr, or less than 2 hr, or less than 1 hr. The reaction time can be selected so that a predetermined conversion can be obtained. When the catalyst is an ionic liquid, the reaction time is a function of the degree of mixing, the reaction temperature, the concentration of the carbocation promoter, the molar ratio of the catalyst promoter to liquid catalyst, and the mass/volume ratio of liquid catalyst to hydrocarbon being reacted. Generally, increasing any of these conditions will increase the reaction rate.

When a liquid catalyst is used, the reaction will proceed simply by contacting the hydrocarbon feed and the liquid catalyst, the reaction rate is generally too slow to be commercially viable. When mass transfer rate is controlling, the reaction rate can be substantially increased by increasing the mixing intensity of hydrocarbon feed and liquid catalyst. After a certain point, increasing the mixing intensity will not provide any additional benefit. Mixing intensity can be controlled using pumps, flow configurations, and baffles. Baffles help to prevent a vortex from forming in the reactor, which would reduce the amount of mixing.

The contacting step may be practiced in laboratory scale experiments through full scale commercial operations. The process may be operated in batch, continuous, or semi-continuous mode. The contacting step can take place in various ways, with both concurrent and co-current flow processes being suitable. The order of addition of the reactants may not always be critical. For example, the reactants can be added individually, or some reactants may be combined or mixed before being combined or mixed with other reactants.

Suitable catalysts include, but are not limited to, HF, sulfated zirconias, $AlCl_2/SiO_2$, zeolites, ionic solids, platinum on chlorided $Al_2O_3/Ga_2O_3$ supports, supported ionic liquids, $Pt/W/Al_2O_3$, $HF/TiF_4$, ionic liquids, or combinations thereof. The first and second catalysts can be the same or different.

When either the first and/or second catalyst is an ionic liquid, when the ionic liquid catalyst is separated from the first and/or second reaction product mixtures, it can include deactivated catalyst after being used in the process. The ionic liquid catalyst becomes deactivated as a result of the buildup of a heavy hydrocarbon, which will be referred to as conjunct polymer herein. This conjunct polymer is a byproduct of the disproportionation and reverse disproportionation reactions. The deactivated catalyst can be regenerated using any known regeneration process. Suitable regeneration methods include, but are not limited to the following. The ionic liquid containing the conjunct polymer could be contacted with a reducing metal (e.g., Al), an inert hydrocarbon (e.g., hexane), and hydrogen and heated to about 100° C. The deactivating polymer will be transferred to the hydrocarbon phase, allowing for the conjunct polymer to be removed from the ionic liquid phase. See e.g., U.S. Pat. No. 7,651,970; U.S. Pat. No. 7,825,055; U.S. Pat. No. 7,956,002; and U.S. Pat. No. 7,732,363. Another method involves contacting the ionic liquid containing the conjunct polymer with a reducing metal (e.g., Al) in the presence of an inert hydrocarbon (e.g. hexane) and heating to about 100° C. The conjunct polymer will be transferred to the hydrocarbon phase, allowing for the conjunct polymer to be removed from the ionic liquid phase. See e.g., U.S. Pat. No. 7,674,739 B2. Still another method of regenerating the ionic liquid involves contacting the ionic liquid containing the conjunct polymer with a reducing metal (e.g., Al), HCl, and an inert hydrocarbon (e.g. hexane), and heating to about 100° C. The conjunct polymer will be transferred to the hydrocarbon phase, allowing for the conjunct polymer to be removed from the IL phase. See e.g., U.S. Pat. No. 7,727,925. The ionic liquid can be regenerated by adding a homogeneous metal hydrogenation catalyst (e.g., $(PPh_3)_3RhCl$) to the ionic liquid containing the conjunct polymer and an inert hydrocarbon (e.g. hexane). Hydrogen would be introduced, and the conjunct polymer would be reduced and transferred to the hydrocarbon layer. See e.g., U.S. Pat. No. 7,678,727. Another method for regenerating the ionic liquid involves adding HCl, isobutane, and an inert hydrocarbon to the ionic liquid containing the conjunct polymer and heating to about 100° C. The conjunct polymer would react to form an uncharged complex, which would transfer to the hydrocarbon phase. See e.g., U.S. Pat. No. 7,674,740. The ionic liquid could also be regenerated by adding a supported metal hydrogenation catalyst (e.g. Pd/C) to the ionic liquid containing the conjunct polymer and an inert hydrocarbon (e.g. hexane). Hydrogen would be introduced and the conjunct polymer would be reduced and transferred to the hydrocarbon layer. See e.g., U.S. Pat. No. 7,691,771. Still another method involves adding a suitable substrate (e.g. pyridine) to the ionic liquid containing the conjunct polymer. After a period of time, an inert hydrocarbon would be added to wash away the liberated conjunct polymer. The ionic liquid precursor [1-butyl-1-methylpyrrolidinium][Cl] would be added to the ionic liquid (e.g. [1-butyl-1-methylpyrrolidinium][Al2Cl7]) containing the conjunct polymer followed by an inert hydrocarbon. After a given time of mixing, the hydrocarbon layer would be separated, resulting in a regenerated ionic liquid. The solid residue would be converted to ionic liquid by adding $AlCl_3$. See e.g., U.S. Pat. No. 7,737,363 and U.S. Pat. No. 7,737,067. Another method involves adding the ionic liquid containing the conjunct polymer to a suitable substrate (e.g. pyridine) and an electrochemical cell containing two aluminum electrodes and an inert hydrocarbon. A voltage would be applied and the current measured to determine the extent of reduction. After a given time, the inert hydrocarbon would be separated, resulting in a regenerated ionic liquid. See, e.g., U.S. Pat. No. 8,524,623.

In some embodiments, after the ionic liquid has been regenerated, a carbocation promoter is added to the regenerated ionic liquid so the liquid catalyst can be recycled to the reaction zone.

The molar ratio of the carbocation promoter to the ionic liquid in the liquid catalyst is typically in the range of about 0:1 to about 3:1, or about 0.1:1 to about 1:1. This relates to forming the carbocation promoter from the halo-alkane or mineral acid. This ratio is important relative to the specific type of anion. For example, if the anion is $AlCl_4^-$, a reaction is unlikely to occur or will be poor because the aluminum is fully coordinated. However, if the anion is $Al_2Cl_7^-$, there is some aluminum present that can coordinate to the carbocation promoter's anion, assisting in generating the carbocation from the carbocation promoter.

When an ionic liquid catalyst is used the mass or volume ratio of liquid catalyst (ionic liquid and carbocation promoter) to hydrocarbon feed is typically less than about 1:1. This is desirable because the ionic liquid is an expensive component in the process. In some embodiments, the mass ratio of ionic liquid to hydrocarbon feed is not more than about 0.75:1, or not more than about 0.7:1, or not more than about 0.65:1, or not more than about 0.60:1, or not more than about 0.55:1, or not more than about 0.50:1. In some embodiments, the volume ratio of ionic liquid to hydrocarbon feed is not more than about 0.8:1, or not more than about 0.7:1, or not more than about 0.6:1, or not more than about 0.5:1, or not more than about 0.45:1, or not more than about 0.4:1, or not more than about 0.35:1, or not more than about 0.3:1, or not more than about 0.25:1. In some embodiments, the mass or volume ratios of liquid catalyst to hydrocarbon feed can be about 1:1 or more.

When an ionic liquid catalyst is used, there can be one or more ionic liquids in the liquid catalyst. If both the first and second catalysts use ionic liquids, the ionic liquids in the first and second liquid catalysts can be the same or different, as can the carbocation precursors.

In some embodiments, the liquid catalyst comprises an ionic liquid and a carbocation promoter. The ionic liquid is in liquid form. In some embodiments, it is not supported on an oxide support. In addition, in some embodiments, the ionic liquids do not contain Brønsted acids, so the acid concentration within these systems is less than prior art processes using ionic liquids which are Brønsted acidic organic cations. In some embodiments, the acid concentration is less than about 2.5 M, or less than about 2.25 M, or less than about 2.0 M, or less than about 1.75 M, or less than about 1.5 M.

The ionic liquid comprises an organic cation and an anion. Suitable organic cations include, but are not limited to:

where $R^1$-$R^{21}$ are independently selected from $C_1$-$C_{20}$ hydrocarbons, $C_1$-$C_{20}$ hydrocarbon derivatives, halogens, and H. Suitable hydrocarbons and hydrocarbon derivatives include saturated and unsaturated hydrocarbons, halogen substituted and partially substituted hydrocarbons and mixtures thereof. $C_1$-$C_8$ hydrocarbons are particularly suitable.

The anion can be derived from halides, sulfates, bisulfates, nitrates, sulfonates, fluoroalkanesulfonates, and combinations thereof. The anion is typically derived from metal and nonmetal halides, such as metal and nonmetal chlorides, bromides, iodides, fluorides, or combinations thereof. Combinations of halides include, but are not limited to, mixtures of two or more metal or nonmetal halides (e.g., $AlCl_4^-$ and $BF_4^-$), and mixtures of two or more halides with a single metal or nonmetal (e.g., $AlCl_3Br$). In some embodiments, the metal is aluminum, with the mole fraction of aluminum ranging from 0<Al<0.25 in the anion. Suitable anions include, but are not limited to, $AlCl_4^-$, $Al_2Cl_7^-$, $Al_3Cl_{10}^-$, $AlCl_3Br^-$, $Al_2Cl_6Br^-$, $Al_3Cl_9Br^-$, $AlBr_4^-$, $Al_2Br_7^-$, $Al_3Br_{10}^-$, $GaCl_4^-$, $Ga_2Cl_7^-$, $Ga_3Cl_{10}^-$, $GaCl_3Br^-$, $Ga_2Cl_6Br^-$, $Ga_3Cl_9Br^-$, $CuCl_2^-$, $Cu_2Cl_3^-$, $Cu_3Cl_4^-$, $ZnCl_3^-$, $FeCl_3^-$, $FeCl_4^-$, $Fe_3Cl_7^-$, $PF_6^-$, and $BF_4^-$.

The ionic liquid is typically combined with one or more carbocation promoters. In some embodiments, the carbocation promoter is added to the ionic liquid. In other embodiments, the carbocation promoter is generated in situ. However, in situ production might not provide reproducible results if it is not controlled.

Suitable carbocation promoters include, but are not limited to, halo-alkanes, mineral acids alone or combined with alkenes, and combinations thereof. Suitable halo-alkanes include but are not limited to 2-chloro-2-methylpropane, 2-chloropropane, 2-chlorobutane, 2-chloro-2-methylbutane, 2-chloropentane, 1-chlorohexane, 3-chloro-3-methylpentane, perchloroethylene, hydrogen chloride, or combinations thereof. In some embodiments, the carbocation promoters are not cyclic alkanes.

Suitable mineral acids include, but are not limited to, HCl, HBr, $H_2SO_4$, and $HNO_3$. Although HF can also be used, it is less desirable due to safety issues. If the mineral acid is not strong enough to protonate off a hydrogen from a C—H bond, isobutene or another alkene can be added with the mineral acid to produce the desired carbocation promoter. The mineral acid can be generated in situ by the addition of a compound that reacts with the ionic liquid. In situ acid generation can also occur as a result of reaction with water present in the system. The mineral acid may also be present as an impurity in the ionic liquid.

The $C_{8+}$-rich fraction can be sent to a reforming zone. The reforming zone upgrades the octane number of the reforming feed stream through a variety of reactions including naphthene dehydrogenation and paraffin dehydrocyclization and isomerization.

Reforming operating conditions may include a pressure of from about atmospheric to about 6080 kPa(a), with the preferred range being from atmospheric to about 2026 kPa(a) and a pressure of below 1013 kPa(a) being especially preferred. Hydrogen is generated within the reforming zone, but additional hydrogen may be directed, if necessary, to the reforming zone in an amount sufficient to correspond to a ratio of from about 0.1 to 10 moles of hydrogen, both generated and added, per mole of hydrocarbon feedstock. The volume of the contained reforming catalyst corresponds to a liquid hourly space velocity of from about 1 to 40 hr$^{-1}$. The operating temperature generally is in the range of 260° to 560° C.

Reforming catalysts may comprise a supported platinum-group metal component which comprises one or more platinum-group metals, with a platinum component being preferred. An illustrative platinum component generally comprises from about 0.01 to 2 mass of the catalytic composite, preferably 0.05 to 1 mass %, calculated on an elemental basis. Reforming catalysts may contain other metal components known to modify the effect of the preferred platinum component. Such metal modifiers may include Group IVA (14) metals, other Group VIII (8-10) metals, rhenium, indium, gallium, zinc, uranium, dysprosium, thallium and mixtures thereof. A preferred metal modifier is a tin component. Catalytically effective amounts of such metal modifiers may be incorporated into the catalyst by any means known in the art.

The reforming catalyst may be a dual-function composite containing a metallic hydrogenation-dehydrogenation component on a refractory support which provides acid sites for cracking and isomerization. The refractory support of the reforming catalyst should be a porous, adsorptive, high-surface-area material which is uniform in composition without composition gradients of the species inherent to its composition. Examples of suitable refractory supports are those containing one or more of: (1) refractory inorganic oxides such as alumina, silica, titania, magnesia, zirconia, chromia, thoria, boria or mixtures thereof; (2) synthetically prepared or naturally occurring clays and silicates, which may be acid-treated; (3) crystalline zeolitic aluminosilicates, either naturally occurring or synthetically prepared such as FAU, MEL, MFI, MOR, MTW (IUPAC Commission on Zeolite Nomenclature), in hydrogen form or in a form which has been exchanged with metal cations; (4) non-zeolitic molecular sieves as disclosed in U.S. Pat. No. 4,741,820, incorporated by reference; (5) spinels such as $MgAl_2O_4$, $FeAl_2O_4$, $ZnAl_2O_4$, $CaAl_2O_4$; and (6) combinations of materials from one or more of these groups.

Reforming catalysts may optimally contain a halogen component. The halogen component may be fluorine, chlorine, bromine or iodine or mixtures thereof. Chlorine is the preferred halogen component.

The reforming catalyst may comprise a large-pore molecular sieve such as a molecular sieve having an effective pore diameter of about 7 angstroms or larger. Examples of large-pore molecular sieves which might be incorporated into the present catalyst include LTL, FAU, AFI and MAZ (IUPAC Commission on Zeolite Nomenclature) and zeolite-beta. Or, the reforming catalyst may contain a nonacidic L-zeolite (LTL) and an alkali-metal component as well as a platinum-group metal component. It is often necessary to composite the L-zeolite with a binder in order to provide a convenient form. Any refractory inorganic oxide binder is suitable. One or more of silica, alumina or magnesia may be preferred binder materials. The L-zeolite and binder may be composited to form the desired catalyst shape by any method known in the art. An alkali metal component is part of the alternative reforming catalyst. One or more of the alkali metals, including lithium, sodium, potassium, rubidium, cesium and mixtures thereof, may be used, with potassium being preferred. The alkali metal optimally will occupy essentially all of the cationic exchangeable sites of the nonacidic L-zeolite.

The iso-$C_4$-rich product can be sent to an alkylation zone. Alkylation is typically used to combine light olefins, for example mixtures of alkenes such as propylene and butylene, with isobutane to produce a relatively high-octane branched-chain paraffinic hydrocarbon fuel, including isoheptane and isooctane. Similarly, an alkylation reaction can be performed using an aromatic compound such as benzene in place of the isobutane. When using benzene, the product resulting from the alkylation reaction is an alkylbenzene (e.g. toluene, xylenes, ethylbenzene, etc.). For isobutene alkylation, typically, the reactants are mixed in the presence of a strong acid catalyst, such as sulfuric acid or hydrofluoric acid. The alkylation reaction is carried out at mild temperatures, and is typically a two-phase reaction. Because the reaction is exothermic, cooling is needed. Depending on the catalyst used, normal refinery cooling water provides sufficient cooling. Alternatively, a chilled cooling medium can be provided to cool the reaction. The catalyst protonates the alkenes to produce reactive carbocations which alkylate the isobutane reactant, thus forming branched chain paraffins from isobutane. Aromatic alkylation is generally now conducted with solid acid catalysts including zeolites or amorphous silica-aluminas.

The alkylation reaction zone is maintained at a pressure sufficient to maintain the reactants in liquid phase. For a hydrofluoric acid catalyst, a general range of operating pressures is from about 200 to about 7100 kPa absolute. The temperature range covered by this set of conditions is from about −20° C. to about 200° C. For at least alkylation of aromatic compounds, the volumetric ratio of hydrofluoric acid to the total amount of hydrocarbons entering the reactor should be maintained within the broad range of from about 0.2:1 to about 10:1, preferably from about 0.5:1 to about 2:1

Any suitable alkylation catalyst may be used. Typically, the catalysts are acidic. Suitable alkylation catalysts include, but are not limited to, hydrofluoric acid, sulfuric acid and acidic ionic liquids. Other catalysts include zeolites having a zeolite framework type selected from the groups consisting of beta, MOR, MWW, FAU and NES. Suitable zeolites include mordenite, ZSM-4, ZSM-12, ZSM-20, offretite, gmelinite, beta, NU-87, UZM-8, MCM-22, MCM-36, MCM-49, zeolite Y, zeolite X, and gottardite. Another class of acidic, solid catalysts are acidified refractory oxides such as chlorided, fluorided, or sulfated alumina, gallia, boria, molybdia, ytterbia, titania, chromia, silica, zirconia, and the like and combinations thereof. Clays and amorphous catalysts may also find utility. Further discussion of alkylation catalysts can be found in U.S. Pat. Nos. 5,196,574; 6,315, 964B1 and 6,617,481B1. Newer alkylation catalysts can also be used in this process. For example, one such catalyst comprises a mixture of two types of zeolitic materials, where the zeolites are mixed and produced to have two zeolites within a single catalyst pellet. With the new catalysts, the first zeolite is also characterized by its acidity, wherein the acidity is characterized by having less than 70% of $NH_3$ desorption off the zeolite at temperatures greater than 400° C. An example of the first zeolite is UZM-8. The second zeolite having a silica to alumina molar ratio less than 8, and includes a rare earth element incorporated into the zeolitic framework in an amount greater than 16.5 wt %. The first zeolite component is in an amount between 10 and 90% by weight of the catalyst, and the second zeolite component is in an amount between 10 and 90% by weight. The zeolites are intermingled into single catalyst particles. An example of the second zeolite is a rare earth substituted X zeolite, Y zeolite, or a zeolite having an EMT/FAU intergrowth. The incorporation of rare earth exchanged ions in a low ratio zeolite reduces the acidity due to an increase in the number of framework alumina at low ratios, and also reduces geometric space in the supercage.

The $C_6$-rich fraction can be isomerized to convert the normal paraffins to branched paraffins. The feed mixture may be contacted with the isomerization catalyst at suitable isomerization conditions. Generally, such conditions include a pressure of from about 700 kPaa to about 7000 kPaa and at an elevated temperature as required by the activity of the catalyst. The temperature are typically between 40° C. and 235° C. The liquid hourly space velocity is typically between 0.5 and 12 $hr^{-1}$.

The catalyst composites that can be used in the isomerization zone include traditional isomerization catalysts including chlorided platinum alumina, crystalline aluminosilicates or zeolites, and other solid strong acid catalysts such as sulfated zirconia and modified sulfated zirconia. Crystalline aluminosilicate or crystalline zeolite catalysts can be used. The zeolitic catalyst can comprise a Group VIII noble metal, a hydrogen form crystalline aluminosilicate, and a refractory inorganic oxide with the catalyst composition having a surface area of at least 580 $m^2/g$. The Group VIII noble metal is typically present in an amount from about 0.01 to 5% by weight of the composite and preferably in an amount of at least 0.15% by weight but not over 0.35% by weight. The zeolitic catalytic composite may also contain a catalytically effective amount of a promoter metal such as tin, lead, germanium, cobalt, nickel, iron, tungsten, chromium, molybdenum, bismuth, indium, gallium, cadmium, zinc, uranium, copper, silver, gold, tantalum, or one or more of rare earth metals and mixtures thereof. The hydrogen-formed silica alumina has either a three-dimensional or channel pore structure crystal lattice framework. The three-dimensional aluminosilicates include both synthetic and naturally occurring silica aluminas such as faujasites, which include X-type, Y-type, ultrastable-Y, and the like. L-type, omega-type, and mordenite are examples of the channel pore structure crystalline aluminosilicates. Mordenite, in either naturally occurring or synthetic form are one embodiment, particularly with a silica to alumina ratio of at least 16:1. The hydrogen form aluminosilicate may be present in an amount within the range of 50 to about 99.5 wt-%, preferably within the range of 75 to about 95 wt-%, and a refractory inorganic oxide may be present in an amount within the range of from 25 to about 50 wt-%. Another suitable isomerization catalyst is a solid strong acid catalyst which comprises a sulfated support of an oxide or hydroxide of a Group IVB (IUPAC 4) metal, preferably zirconium oxide or hydroxide, at least a first component which is a lanthanide element or yttrium component, and at least a second component being a platinum-group metal component. The catalyst optionally contains an inorganic-oxide binder, especially alumina. The support material of the solid strong acid catalyst comprises an oxide or hydroxide of a Group IVB (IUPAC 4). Sulfate is composited on the support material. A component of a lanthanide-series element is incorporated into the composite by any suitable means. Suitable amounts of the lanthanide series element component are in the range of about 0.01 to about 10 mass-% on an elemental basis, of the catalyst. A platinum-group metal component is added to the catalytic composite by any means known in the art to effect the catalyst of the invention, e.g., by impregnation. The platinum-group metal component may be selected from the group consisting of platinum, palladium, ruthenium, rhodium, iridium, or osmium. Amounts in the range of from about 0.01 to about 2 wt-% platinum-group metal component, on an elemental basis are suitable. Optionally, the catalyst is bound with a refractory inorganic oxide. The binder, when employed, usually comprises from about 0.1 to 50 mass-%, preferably from about 5 to 20 mass-%, of the finished catalyst. Examples of suitable atomic ratios of lanthanide or yttrium to platinum-group metal for this catalyst is at least about 1:1; about 2:1 or greater; and about 5:1 or greater. The catalyst may optionally further include a third component of iron, cobalt, nickel, rhenium or mixtures thereof. For example, iron may be present in amounts ranging from about 0.1 to about 5 wt-% on an elemental basis. Another class of suitable isomerization catalysts for this invention is the chlorided platinum alumina catalysts. The aluminum is preferably an anhydrous gamma-alumina with a high degree of purity. The catalyst may also contain other platinum group metals. The term "platinum group metals" refers to noble metals excluding silver and gold which are selected from the group consisting of platinum, palladium, germanium, ruthenium, rhodium, osmium, and iridium. These metals demonstrate differences in activity and selectivity such that platinum has now been found to be the most suitable for this process. The catalyst will contain from about 0.1 to 0.25 wt-% of the platinum. Other platinum group metals may be present in a concentration of from 0.1 to 0.25 wt-%. The platinum component may exist within the final catalytic composite as an oxide or halide or as an elemental metal. The presence of the platinum component in its reduced state has been found most suitable for this process. The chloride component termed in the art "a combined chloride" is present in an amount from about 2 to about 10 wt-% based upon the dry support material. The inorganic oxide preferably comprises alumina and more preferably gamma-alumina, eta-alumina, and mixtures thereof.

EXAMPLE 1

Experimental Set Up

The set-up included a 300 mL autoclave equipped with a mechanical stirrer, pressure gauge, thermocouple, dipleg, rupture disc and valves to introduce the feed and withdraw an aliquot for GC analysis. The rupture disc vented to a knock out pot. The house nitrogen passed through a pressure regulator to a high surface sodium column and was then split: feeding to the charger for feed introduction or to a line for various uses (i.e., 2-methyl-2-chloropropane/$C_5P$ introduction). The dipleg was constructed such that the height positions it in the paraffin layer. Upon opening the valve, the withdrawn paraffin layer passed through a column of silica, to the GC valve and then through a metering valve into a waste container. The reaction mixture was analyzed using the ASTM UOP690-99 method.

EXAMPLE 2 iC5 [("Bu)$_3$P(Hex)][Al$_2$Cl$_6$Br] in Hastelloy C Autoclave at 95° C.

A 300 mL Hastelloy C autoclave, Hastelloy C baffle, and 75 mL stainless steel sample cylinder were dried in a 120° C. oven for at least 8 h. The dried autoclave and sample cylinder were brought into a nitrogen glovebox and allowed to cool to ambient temperature. The autoclave was charged with 50.419 g of [tributyl(hexyl)phosphonium][Al$_2$Cl$_6$Br] ([("Bu)$_3$P(Hex)][Al$_2$Cl$_6$Br]), and the autoclave head was attached. To the sample cylinder 3.680 g of 2-chloro-2-methylpropane, which had previously been dried over activated sieves, was added. The sample cylinder was closed under nitrogen, and both the autoclave and sample cylinder were removed from the glovebox. The autoclave was charged with 102 g of iso-pentane from a pressurized feed charger without displacing the nitrogen present in the autoclave. The iso-pentane passed over a high surface sodium column to remove any water before entering the autoclave. Similarly, the nitrogen used to pressurize the charger and for all other work passed over a separate high surface sodium column. The sample cylinder was charged with 15 g of iso-pentane using the same method described above and then attached to the autoclave. The autoclave was heated to 95° C., and the 2-chloro-2-methylpropane/iso-pentane solution in the sample cylinder was added with an over-pressure of nitrogen. After complete addition, the initial pressure in the autoclave was 165 psi (1.138 MPa), and the autoclave was set to stir at 1700 rpm. The reaction was monitored periodically by GC. In order to analyze the paraffinic layer, the stirring was stopped, and the product was allowed to settle for 5 minutes. An aliquot was sampled directly from the autoclave by opening a valve from the autoclave, passing the paraffinic layer through a SiO$_2$ column, and then passing it directly into a GC sample loop. The results of the run are shown in Tables 1 and 2.

TABLE 1

Disproportionation and Isomerization of iso-Pentane at 95° C., wt. % of reaction mixture

| t (h) | % Conv. | C3− | iC4 | nC4 | iC5 | nC5 | C6P | C7+ |
|---|---|---|---|---|---|---|---|---|
| 0.6 | 72 | 0.37 | 27.78 | 1.72 | 28.32 | 4.2 | 16.21 | 21.36 |
| 1.8 | 76 | 0.82 | 31.73 | 3.91 | 23.66 | 5.4 | 17.15 | 17.29 |
| 3.1 | 77 | 1.05 | 31.50 | 5.12 | 23.14 | 5.71 | 17.1 | 16.38 |
| 4.6 | 77 | 1.21 | 31.56 | 6.14 | 22.79 | 5.90 | 16.91 | 15.42 |

TABLE 2

| | Time (h) | | | | |
|---|---|---|---|---|---|
| | 0.6 | 1.8 | 3.1 | 4.6 | NA |
| Wt. % | | | | | feed |
| C3P | 0.37 | 0.82 | 1.05 | 1.21 | 0.00 |
| C4P | 29.50 | 35.64 | 36.62 | 37.70 | 0.00 |
| C5P | 32.51 | 29.06 | 28.85 | 28.69 | 99.86 |
| C6P | 16.22 | 17.16 | 17.10 | 16.91 | 0.00 |
| C7P | 7.66 | 8.19 | 7.96 | 7.56 | 0.00 |
| C8P | 3.42 | 3.88 | 3.79 | 3.57 | 0.00 |
| C9+ | 9.74 | 4.63 | 4.04 | 3.81 | 0.00 |
| C5N | 0.00 | 0.00 | 0.00 | 0.00 | 0.00 |

TABLE 2-continued

|  | Time (h) | | | | |
| --- | --- | --- | --- | --- | --- |
|  | 0.6 | 1.8 | 3.1 | 4.6 | NA |
| C6N | 0.00 | 0.00 | 0.00 | 0.00 | 0.00 |
| C7N | 0.01 | 0.02 | 0.02 | 0.02 | 0.00 |
| C8N | 0.51 | 0.56 | 0.53 | 0.48 | 0.00 |
| C6A | 0.00 | 0.00 | 0.00 | 0.00 | 0.00 |
| C7A | 0.04 | 0.04 | 0.04 | 0.03 | 0.00 |
| C8A | 0.01 | 0.02 | 0.02 | 0.02 | 0.00 |
| nC4-nC5 unknowns | 0.00 | 0.00 | 0.00 | 0.00 | 0.14 |
| mmoles (based on wt. %) | | | | | |
| C3P | 8 | 19 | 24 | 27 | 0 |
| C4P | 508 | 613 | 630 | 649 | 0 |
| C5P | 451 | 403 | 400 | 398 | 1384 |
| C6P | 188 | 199 | 198 | 196 | 0 |
| C7P | 76 | 82 | 79 | 75 | 0 |
| C8P | 30 | 34 | 33 | 31 | 0 |
| C9+ | 76 | 36 | 31 | 30 | 0 |
| C5N | 0 | 0 | 0 | 0 | 0 |
| C6N | 0 | 0 | 0 | 0 | 0 |
| C7N | 0 | 0 | 0 | 0 | 0 |
| C8N | 5 | 5 | 5 | 4 | 0 |
| C6A | 0 | 0 | 0 | 0 | 0 |
| C7A | 0 | 0 | 0 | 0 | 0 |
| C8A | 0 | 0 | 0 | 0 | 0 |
| nC4-nC5 unknowns | 0 | 0 | 0 | 0 | 2 |
| Total mmoles | 1343 | 1391 | 1402 | 1411 | 1386 |

EXAMPLE 3 nC5 with [1-butyl-1-methylpyrrolidinium][Al$_2$Cl$_7$] at 95° C.

A 300 mL Hastelloy C autoclave, Hastelloy C baffle, and 75 mL stainless steel sample cylinder were dried in a 120° C. oven for at least 8 h. The dried autoclave and sample cylinder were brought into a nitrogen glovebox and allowed to cool to ambient temperature. The autoclave was charged with 52.795 g of [1-butyl-1-methylpyrrolidinium][Al$_2$Cl$_7$] and the autoclave head was attached. To the sample cylinder 5.24 g of 2-chloro-2-methylpropane, which had previously been dried over activated sieves, was added. The sample cylinder was closed under nitrogen, and both the autoclave and sample cylinder were removed from the glovebox. The autoclave was charged with 98 g of n-pentane from a pressurized feed charger without displacing the nitrogen present in the autoclave. The n-pentane passed over a high surface sodium column to remove any water before entering the autoclave. Similarly, the nitrogen used to pressurize the charger and for all other work passed over a separate high surface sodium column. The sample cylinder was charged with 33 g of n-pentane using the same method described above and attached to the autoclave. The autoclave was heated to 95° C., and the 2-chloro-2-methylpropane/n-pentane solution in the sample cylinder was added with an over-pressure of nitrogen. After complete addition, the initial pressure in the autoclave was 260 psi (1.793 MPa), and the autoclave was set to stir at 1700 rpm. The reaction was monitored periodically by GC. In order to analyze the paraffinic layer, the stirring was stopped, and the product was allowed to settle for 5 minutes. An aliquot was sampled directly from the autoclave by opening a valve from the autoclave, passing the paraffinic layer through a SiO$_2$ column, and then passing it directly into a GC sample loop. The results of the run are shown in Tables 3 and 4.

TABLE 3

Disproportionation and Isomerization of n-Pentane at 95° C. with [1-butyl-1-methylpyrrolidinium][Al$_2$Cl$_7$], wt. % of reaction mixture

| t (h) | % Conv. | C3− | iC4 | nC4 | iC5 | nC5 | C6P | C7+ |
| --- | --- | --- | --- | --- | --- | --- | --- | --- |
| 0.6 | 57 | 0.49 | 18.16 | 2.44 | 18.55 | 42.87 | 10.02 | 7.48 |
| 1.9 | 84 | 1.22 | 28.59 | 5.73 | 22.01 | 15.60 | 14.75 | 12.00 |
| 3.2 | 89 | 1.70 | 30.42 | 7.70 | 21.66 | 10.57 | 15.38 | 12.54 |
| 4.4 | 91 | 1.96 | 30.79 | 8.72 | 21.31 | 9.06 | 15.51 | 12.65 |

TABLE 4

| Time (h) | 0.6 | 1.9 | 3.2 | 4.4 | NA |
| --- | --- | --- | --- | --- | --- |
| Wt. % | | | | | feed |
| C3P | 0.49 | 1.22 | 1.70 | 1.96 | 0.00 |
| C4P | 20.60 | 34.32 | 38.12 | 39.51 | 0.00 |
| C5P | 61.41 | 37.61 | 32.23 | 30.37 | 99.60 |
| C6P | 10.02 | 14.76 | 15.39 | 15.50 | 0.00 |
| C7P | 3.93 | 6.04 | 6.24 | 6.25 | 0.00 |
| C8P | 1.52 | 2.64 | 2.85 | 2.89 | 0.00 |
| C9+ | 1.71 | 2.97 | 3.00 | 3.05 | 0.00 |
| C5N | 0.00 | 0.00 | 0.00 | 0.00 | 0.00 |
| C6N | 0.00 | 0.00 | 0.00 | 0.00 | 0.00 |
| C7N | 0.01 | 0.01 | 0.02 | 0.02 | 0.00 |
| C8N | 0.25 | 0.39 | 0.41 | 0.41 | 0.00 |
| C6A | 0.00 | 0.00 | 0.00 | 0.00 | 0.00 |
| C7A | 0.01 | 0.02 | 0.02 | 0.02 | 0.00 |
| C8A | 0.04 | 0.01 | 0.02 | 0.02 | 0.00 |
| nC4-nC5 unknowns | 0.00 | 0.00 | 0.00 | 0.00 | 0.34 |
| nC5-nC6 unknowns | 0.00 | 0.00 | 0.00 | 0.00 | 0.05 |
| mmoles (based on wt. %) | | | | | |
| C3P | 11 | 28 | 39 | 44 | 0 |
| C4P | 354 | 591 | 656 | 680 | 0 |
| C5P | 851 | 521 | 447 | 421 | 1380 |
| C6P | 116 | 171 | 179 | 180 | 0 |
| C7P | 39 | 60 | 62 | 62 | 0 |
| C8P | 13 | 23 | 25 | 25 | 0 |
| C9+ | 13 | 23 | 23 | 24 | 0 |
| C5N | 0 | 0 | 0 | 0 | 0 |
| C6N | 0 | 0 | 0 | 0 | 0 |
| C7N | 0 | 0 | 0 | 0 | 0 |
| C8N | 2 | 4 | 4 | 4 | 0 |
| C6A | 0 | 0 | 0 | 0 | 0 |
| C7A | 0 | 0 | 0 | 0 | 0 |
| C8A | 0 | 0 | 0 | 0 | 0 |
| nC4-nC5 unknowns | 0 | 0 | 0 | 0 | 5 |
| nC5-nC6 unknowns | 0 | 0 | 0 | 0 | 1 |
| Total mmoles | 1402 | 1421 | 1435 | 1441 | 1386 |

EXAMPLE 4

A refinery model was used to estimate the process yields that could be achieved when operating the flexible process on different feedstocks during two different time periods. In this example, the refiner processed a feedstock composed of 50 wt-% butanes and 50 wt-% heptanes in the winter season using reverse disproportotionation to upgrade the butanes to C$_{5+}$ liquid and convert the heptanes to lower aromatic gasoline blendstock. In the summer months, the same process was used to process excess pentanes. A disproportionation mode of operation was used to convert the pentanes to isobutane for use as alkylation feedstock and a C$_{6+}$ gasoline blendstock. Both winter and summer operations used ionic liquid as the catalyst.

WINTER OPERATION—Reverse disproportionation conditions were employed that included a pressure of 2.8 MPa(g) (400 psig), a temperature of 100° C., and a residence time of greater than 4 hours using an ionic liquid catalyst. To maximize the combined yield of $C_{6+}$ blendstock and $iC_4$ for use as alkylation feedstock, the normal butane and pentane co-products produced by the process were recovered and recycled to the reactor. The mass ratio of recycle flow to feedstock was 0.5. Sufficient mechanical mixing was assumed to allow the reactants to approach an equilibrium product mixture. The resultant process mass balance is illustrated in Table 3 below.

TABLE 5

Estimated Process Mass Balance

|  | Wt-% |
|---|---|
| Feed | |
| nC4 | 50 |
| nC7 | 50 |
| Products | |
| C3− | 3.0 |
| iC4 | 40.0 |
| nC4 | 0.1 |
| C5 | 0.2 |
| C6+ | 56.7 |

SUMMER OPERATION—The disproportionation conditions employed included a pressure of 2.8 MPa(g) (400 psig), a temperature of 100° C., and a residence time of greater than 4 hours using an ionic liquid catalyst. To maximize the combined yield of $C_{6+}$ blendstock and $iC_4$ for use as alkylation feedstock, the normal butane and pentane co-products produced by the process were recovered and recycled to the reactor. The volume ratio of recycle flow to feedstock was 0.52. Sufficient mechanical mixing was assumed to allow the reactants to approach an equilibrium product mixture. By recycling unconverted $C_5s$, nearly complete conversion of $C_5s$ was achieved. The net products were 52 vol-% $iC_4$ and 49 vol-% $C_{6+}$ gasoline blend stock. Blending the small amounts of co-product $nC_4$ and $C_5$ with the $C_{6+}$ product increase the gasoline blendstock yield to 49.8 volume-% with an acceptable 45.5 kPaa (6.6 psia) RVP with (R+M)/2 octane rating of about 78. Overall volume swell across the process was about 2% making the operation profitable. The overall process volume balance is illustrated in Table 4 below.

TABLE 6

Estimated Volumetric Yields for C5 Conversion

|  | Vol-% |
|---|---|
| Feed | |
| iC5 | 50 |
| nC5 | 50 |
| Products | |
| C3− | 0.2 |
| iC4 | 52.0 |
| nC4 | 0.2 |
| C5 | 0.4 |
| C6+ | 49.2 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for refining naphtha comprising:
during a first time period:
separating a hydrotreated heavy naphtha feed into a $C_7$-rich fraction and a $C_{8+}$-rich fraction in a first separation zone;
introducing the $C_7$-rich fraction into a first reaction zone;
introducing a stream comprising $C_4$ paraffins into the first reaction zone;
disproportionating a first portion of the $C_7$-rich fraction by contacting the first portion of the $C_7$-rich fraction with a first catalyst in the reaction zone and reverse disproportionating a second portion of the $C_7$-rich fraction and the $C_4$ paraffins by contacting the second portion of the $C_7$-rich fraction and the $C_4$ paraffins with the first catalyst in the first reaction zone under first reaction conditions suitable for disproportionation and reverse disproportionation to form a first reaction product mixture wherein said reverse disproportionating is in a same reaction zone as said disproportionating;
separating the first reaction product mixture in a second separation zone into at least a $C_{3-}$-rich stream, an iso-$C_4$-rich stream, and a $C_{6+}$-rich stream; and
introducing the $C_{6+}$-rich stream into a first hydrocarbon pool comprising $C_4$ to $C_6$ hydrocarbons; and
during a second time period:
separating a hydrotreated light naphtha feed into a $C_5$-rich fraction and a $C_6$-rich fraction;
introducing the $C_5$-rich fraction into a second reaction zone;
disproportionating the $C_5$-rich fraction by contacting the $C_5$-rich fraction with a second catalyst in the second reaction zone under second reaction conditions to form a second reaction product mixture;
separating the second reaction product mixture into at least an iso-$C_4$-rich stream, and a $C_{6+}$-rich stream in a third separation zone; and
introducing the $C_{6+}$-rich stream into a second hydrocarbon pool comprising $C_4$ to $C_6$ hydrocarbons.

2. The process of claim 1 further comprising:
during the first time period, reforming the $C_{8+}$-rich fraction in a reforming zone to form a higher octane reformed product and introducing the reformed product into the first hydrocarbon pool, or
during the second time period, isomerizing the $C_6$-rich fraction in an isomerization zone to form a higher octane isomerized product and introducing the isomerized product into the second hydrocarbon pool.

3. The process of claim 1 wherein:
during the first time period, separating the first reaction product mixture comprises separating the first reaction product mixture into at least the $C_{3-}$-rich stream, the iso-$C_4$-rich stream, a $C_5$-rich stream, and the $C_{6+}$-rich stream, or
during the second time period, separating the second reaction product mixture comprises separating the second reaction product mixture into at least an iso-$C_4$-rich stream, a $C_5$-rich stream, and the $C_{6+}$-rich stream.

4. The process of claim 3 further comprising controlling a vapor pressure of the $C_{6+}$-rich stream by recovering at least a portion of the $C_5$-rich stream during at least one of the first or second time periods.

5. The process of claim 3 further comprising maximizing a gasoline product yield by mixing at least a portion of the $C_5$-rich stream with the $C_{6+}$-rich stream during at least one of the first or second time periods.

6. The process of claim 3 further comprising at least one of recycling at least a portion of the $C_5$-rich stream to the reaction zone during the first period, or recycling at least a portion of the $C_5$-rich stream to the reaction zone during the second time period.

7. The process of claim 1 wherein at least one of the first reaction conditions, or the second reaction conditions includes a temperature of less than about 200° C.

8. The process of claim 1 further comprising introducing the iso-$C_4$-rich stream and at least one olefin containing stream into an alkylation reaction zone during at least one of the first or second time periods to produce low vapor pressure, high octane gasoline blendstock.

9. The process of claim 1 wherein a molar ratio of $C_4$ to $C_7$ is at least 0.055.

10. The process of claim 1 further comprising recycling at least a portion of the iso-$C_4$-rich stream to the reaction zone during at least one of the first or second time periods.

11. The process of claim 1 wherein at least one of the first or second catalyst comprises HF, sulfated zirconias, $AlCl_2/SiO_2$, zeolites, ionic solids, platinum on chlorided $Al_2O_3/Ga_2O_3$ supports, supported ionic liquids, $Pt/W/Al_2O_3$, $HF/TiF_4$, an ionic liquid, or combinations thereof.

12. The process of claim 1, wherein at least one of the first or second catalyst comprises an ionic liquid and a carbocation promoter.

13. The process of claim 12 wherein at least one ionic liquid comprises an organic cation and an anion, and wherein the organic cation is selected from the group consisting of:

where $R^1$-$R^{21}$ are independently selected from $C_1$-$C_{20}$ hydrocarbons, $C_1$-$C_{20}$ hydrocarbon derivatives, halogens, and H.

14. The process of claim 12 wherein at least one ionic liquid comprises an organic cation and an anion, and wherein the anion is derived from halides, sulfates, bisulfates, nitrates, sulfonates, fluoroalkanesulfonates, or combinations thereof.

15. The process of claim 12 wherein at least one carbocation promoter comprises halo-alkanes, mineral acids, alkenes, or combinations thereof.

16. The process of claim 12 further comprising at least one of mechanically mixing while contacting the $C_7$-rich fraction with the first catalyst and while contacting the $C_7$-rich and the $C_4$ paraffins with the first catalyst, or mechanically mixing while contacting the $C_5$-rich fraction with the second catalyst.

17. The process of claim 1 further comprising:
at least one of separating the first catalyst from the first reaction product mixture before separating the first reaction product mixture, or separating the second catalyst from the second reaction product mixture before separating the second reaction product mixture;
regenerating at least one of the first or second separated catalysts;
optionally, adding a carbocation promoter to the first or second regenerated catalyst; and
recycling at least a portion of the first or second regenerated catalyst to the reaction zone.

18. The process of claim 1 wherein a mass ratio of at least one of the first or second liquid catalysts to the $C_7$ fraction and the butanes is less than 0.75:1.

19. The process of claim 1 wherein the hydrotreated heavy naphtha feed is formed by separating a full range hydrotreated naphtha feed into a hydrotreated light naphtha stream and the hydrotreated heavy naphtha feed.

20. A process for refining naphtha comprising:
during a first time period:
separating a hydrotreated heavy naphtha feed into a $C_7$-rich fraction and a $C_{8+}$-rich fraction in a first separation zone;
introducing the $C_7$-rich fraction into a first reaction zone;
introducing a stream comprising $C_4$ paraffins into the first reaction zone;
disproportionating a first portion of the $C_7$-rich fraction by contacting the first portion of the $C_7$-rich fraction with a first liquid catalyst in the reaction zone and reverse disproportionating a second portion of the $C_7$-rich fraction and the $C_4$ paraffins by contacting the second portion of the $C_7$-rich fraction and the $C_4$ paraffins with the first liquid catalyst in the first reaction zone under first reaction conditions suitable for disproportionation and reverse disproportionation to form a first reaction product mixture wherein said reverse disproportionating is in a same reaction zone as said disproportionating, wherein the first liquid catalyst comprises a first unsupported ionic liquid and a first carbocation promoter;
separating the first liquid catalyst from the first reaction product mixture;
separating the first reaction mixture in a second separation zone into at least a $C_{3-}$-rich stream, an iso-$C_4$-rich stream, and a $C_{6+}$-rich stream;
introducing the $C_{6+}$-rich stream into a first hydrocarbon pool; and
reforming the $C_{8+}$-rich fraction in a reforming zone to form a reformed product and introducing the reformed product into the first hydrocarbon pool; and
during a second time period:
separating a light naphtha feed into a $C_5$-rich fraction and a $C_6$-rich fraction;
introducing the $C_5$-rich fraction into a second reaction zone;
disproportionating the $C_5$-rich fraction by contacting the $C_5$-rich fraction with a second liquid catalyst in the second reaction zone under second reaction conditions to form a second reaction product mixture, wherein the second liquid catalyst comprises a second unsupported ionic liquid and a second carbocation promoter;
separating the second liquid catalyst from the second reaction product mixture;

separating the second reaction mixture into at least an iso-$C_4$-rich butane stream, and a $C_{6+}$-rich stream in a third separation zone;

introducing the $C_{6+}$-rich stream into a second hydrocarbon pool; and isomerizing the $C_6$-rich fraction in an isomerization zone and introducing the isomerized product into the second hydrocarbon pool.

\* \* \* \* \*